United States Patent [19]
Lorberboum-Galski et al.

[11] Patent Number: 6,140,066
[45] Date of Patent: Oct. 31, 2000

[54] METHODS OF CANCER DIAGNOSIS USING A CHIMERIC TOXIN

[76] Inventors: Haya Lorberboum-Galski, 723 Bar Kochva Street, Jerusalem 97875; Shai Yarkoni, 33 Lamed Hei Street, Kfar-Saba 44395; Ahmi Ben-Yehudah, Neve Ilan, D.N. Harei Yehuda 90852; Irina Marianovsky, 601/73 Neve Jacob, Jerusalem; Amotz Nechushtan, 214 Banim Street, Ramat Hsharon 47223, all of Israel

[21] Appl. No.: 09/046,992

[22] Filed: Mar. 24, 1998

[51] Int. Cl.[7] .................................................. G01N 33/574
[52] U.S. Cl. ........................... 435/7.23; 435/7.1; 435/7.2; 436/64; 530/398
[58] Field of Search ............................ 435/7.1, 7.2, 7.23; 536/23.1, 23.4; 530/398; 424/1.57, 9.1, 9.34, 9.4, 9.6; 436/64

[56] References Cited

PUBLICATIONS

Nechushtan et al J. Biol. Chem. vol. 272 p. 11597, 1997.
CA 127;16488, 1997.
CA 127:16487, 1997.
CA 126:1325, 1994.

*Primary Examiner*—Sheela Huff
*Attorney, Agent, or Firm*—Pennie & Edmonds

[57] ABSTRACT

The present invention relates to methods for cancer diagnosis using a chimeric toxin. In particular, the invention relates to the use of a chimeric toxin composed of gonadotropin releasing hormone (GnRH) and Pseudomonas exotoxin A (PE) to detect a tumor-associated epitope expressed by human adenocarcinomas. Mutated GnRH-PE molecules that bind but do not kill tumor cells are exemplified.

37 Claims, 7 Drawing Sheets

```
100/1                                    130/11
ATG gag cac tgg tcc tat tgg ctg cgc cct gga gaa gct gga gga gga gga tcc gga gga
MET glu his trp ser tyr trp leu arg pro gly glu ala gly gly gly gly ser gly gly
160/21                                   190/31
gga gga tcc ggt caa gct ttc gac ctc tgg aac gaa tgc gcc aaa gcc tgc gtg ctc gac
gly gly ser gly gln ala phe asp leu trp asn glu cys ala lys ala cys val leu asp
220/41                                   250/51
ctc aag gac ggc gtg cgt tcc agc cgc atg agc gtc gac ccg gcc atc gcc gac acc aac
leu lys asp gly val arg ser ser arg met ser val asp pro ala ile ala asp thr asn
280/61                                   310/71
ggc cag ggc gtg ctg cac tac tcc atg gtc ctg gag ggc ggc aac gac gcg ctc gag ctg
gly gln gly val leu his tyr ser met val leu glu gly gly asn asp ala leu glu leu
340/81                                   370/91
gcc atc gac aac gcc ctc agc atc acc agc gac ggc ctg acc atc cgc ctc gaa ggc ggc
ala ile asp asn ala leu ser ile thr ser asp gly leu thr ile arg leu glu gly gly
400/101                                  430/111
gtc gag ccg aac aag ccg ctg cgc tac agc tac acg cgc cag gcg cgc ggc agg tgg tcg
val glu pro asn lys pro leu arg tyr ser tyr thr arg gln ala arg gly arg trp ser
460/121                                  490/131
ctg aac tgg ctg gta ccg atc ggc cac gag aag ccc tcg aac atc aag gtg ttc atc cac
leu asn trp leu val pro ile gly his glu lys pro ser asn ile lys val phe ile his
520/141                                  550/151
gaa ctg aac gcc ggc aac cag ctc agc cac atg tcg ccg atc tac acc atc gag atg ggc
glu leu asn ala gly asn gln leu ser his met ser pro ile tyr thr ile glu met gly
580/161                                  610/171
gac gag ttg ctg gcg aag ctg gcg cgc gat gcc acc ttc ttc gtc agg gcg cac gag agc
asp glu leu leu ala lys leu ala arg asp ala thr phe phe val arg ala his glu ser
640/181                                  670/191
aac gag atg cag ccg acg ctc gcc atc agc cat gcc ggg gtc agc gtg gtc atg gcc cag
asn glu met gln pro thr leu ala ile ser his ala gly val ser val val met ala gln
700/201                                  730/211
acc cag ccg cgc cgg gaa aag cgc tgg agc gaa tgg gcc agc ggc aag gtg ttg tgc ctg
thr gln pro arg arg glu lys arg trp ser glu trp ala ser gly lys val leu cys leu
760/221                                  790/231
ctc gac ccg ctg gac ggg gtc tac aac tac ctc gcc cag caa cgc tgc aac ctc gac gat
leu asp pro leu asp gly val tyr asn tyr leu ala gln gln arg cys asn leu asp asp
820/241                                  850/251
acc tgg gaa ggc aag atc tac cgg gtg ctc gcc ggc aac ccg gcg aag cat gac ctg gac
thr trp glu gly lys ile tyr arg val leu ala gly asn pro ala lys his asp leu asp
880/261                                  910/271
atc aaa ccc acg gtc atc agt gaa gag ctg gag ttt ccc gag ggc ggc agc ctg gcc gcg
ile lys pro thr val ile ser glu glu leu glu phe pro glu gly gly ser leu ala ala
940/281                                  970/291
ctg acc gcg cac cag gct tgc cac ctg ccg ctg gag act ttc acc cgt cat cgc cag ccg
leu thr ala his gln ala cys his leu pro leu glu thr phe thr arg his arg gln pro
```

FIG.1A

```
1000/301                                1030/311
cgc ggc tgg gaa caa ctg gag cag tgc ggc tat ccg gtg cag cgg ctg gtc gcc ctc tac
arg gly trp glu gln leu glu gln cys gly tyr pro val gln arg leu val ala leu tyr
1060/321                                1090/331
ctg gcg gcg cgg ctg tcg tgg aac cag gtc gac cag gtg atc cgc aac gcc ctg gcc agc
leu ala ala arg leu ser trp asn gln val asp gln val ile arg asn ala leu ala ser
1120/341                                1150/351
ccc ggc agc ggc ggc gac ctg ggc gaa gcg atc cgc gag cag ccg gag cag gcc cgt ctg
pro gly ser gly gly asp leu gly glu ala ile arg glu gln pro glu gln ala arg leu
1180/361                                1210/371
gcc ctg acc ctg gcc gcc gcc gag agc gag cgc ttc gtc cgg cag ggc acc ggc aac gac
ala leu thr leu ala ala ala glu ser glu arg phe val arg gln gly thr gly asn asp
1240/381                                1270/391
gag gcc ggc gcg gcc aac gcc gac gtg gtg agc ctg acc tgc ccg gtc gcc gcc ggt gaa
glu ala gly ala ala asn ala asp val val ser leu thr cys pro val ala ala gly glu
1300/401                                1330/411
tgc gcg ggc ccg gcg gac agc ggc gac gcc ctg ctg gag gcg aac tat ccc act ggc gcg
cys ala gly pro ala asp ser gly asp ala leu leu glu ala asn tyr pro thr gly ala
1360/421                                1390/431
gag ttc ctc ggc gac ggc ggc gac gtc agc ttc agc acc cgc ggc acg cag aac tgg acg
glu phe leu gly asp gly gly asp val ser phe ser thr arg gly thr gln asn trp thr
1420/441                                1450/451
gtg gag cgg ctg ctc cag gcg cac cgc caa ctg gag gag cgc ggc tat gtg ttc gtc ggc
val glu arg leu leu gln ala his arg gln leu glu glu arg gly tyr val phe val gly
1480/461                                1510/471
tac cac ggc acc ttc ctc gaa gcg gcg caa agc atc gtc ttc ggc ggg gtg cgc gcg cgc
tyr his gly thr phe leu glu ala ala gln ser ile val phe gly gly val arg ala arg
1540/481                                1570/491
agc cag gac ctc gac gcg atc tgg cgc ggt ttc tat atc gcc ggc gat ccg gcg ctg gcc
ser gln asp leu asp ala ile trp arg gly phe tyr ile ala gly asp pro ala leu ala
1600/501                                1630/511
tac ggc tac gcc cag gac cag gaa ccc gac gca cgc ggc cgg atc gcg aac ggt gcc ctg
tyr gly tyr ala gln asp gln glu pro asp ala arg gly arg ile arg asn gly ala leu
1660/521                                1690/531
ctg cgg gtc tat gtg ccg cgc tcg agc ctg ccg ggc ttc tac cgc acc agc ctg acc ctg
leu arg val tyr val pro arg ser ser leu pro gly phe tyr arg thr ser leu thr leu
1720/541                                1750/551
gcc gcg ccg gag gcg gcg ggc gag gtc gaa cgg ctg atc ggc cat ccg ctg ccg ctg cgc
ala ala pro glu ala ala gly glu val glu arg leu ile gly his pro leu pro leu arg
1780/561                                1810/571
ctg gac gcc atc acc ggc ccc gag gag gaa ggc ggg cgc ctg gag acc att ctc ggc tgg
leu asp ala ile thr gly pro glu glu glu gly gly arg leu glu thr ile leu gly trp
1840/581                                1870/591
ccg ctg gcc gag cgc acc gtg gtg att ccc tcg gcg atc ccc acc gac ccg cgc aac gtc
pro leu ala glu arg thr val val ile pro ser ala ile pro thr asp pro arg asn val
```

FIG.1B

1900/601                                    1930/611
ggc ggc gac ctc gac ccg tcc agc atc ccc gac aag gaa cag gcg atc agc gcc ctg ccg
gly gly asp leu asp pro ser ser ile pro asp lys glu gln ala ile ser ala leu pro
1960/621                                    1990/631
gac tac gcc agc cag ccc ggc aaa ccg ccg cgc gag gac ctg aag taa
asp tyr ala ser gln pro gly lys pro pro arg glu asp leu lys OCH

FIG.1C

```
100/1                              130/11
ATG gag cac tgg tcc tat tgg ctg cgc cct gga gaa gct gga gga gga gga tcc gga gga
Met glu his trp ser tyr trp leu arg pro gly glu ala gly gly gly gly ser gly gly
160/21                             190/31
gga gga tcc ggt cAA GCT TTT GTT AAC GCC CAT ATG GCC GAA GAG GGC GGC AGC CTG GCC
gly gly ser gly gln ala phe val asn ala his met ala glu glu gly gly ser leu ala
220/41                             250/51
GCG CTG ACC GCG CAC CAG GCT TGC CAC CTG CCG CTG GAG ACT TTC ACC CGT CAT CGC CAG
ala leu thr ala his gln ala cys his leu pro leu glu thr phe thr arg his arg gln
280/61                             310/71
CCG CGC GGC TGG GAA CAA CTG GAG CAG TGC GGC TAT CCG GTG CAG CGG CTG GTC GCC CTC
pro arg gly trp glu gln leu glu gln cys gly tyr pro val gln arg leu val ala leu
340/81                             370/91
TAC CTG GCG GCG CGG CTG TCG TGG AAC CAG GTC GAC CAG GTG ATC CGC AAC GCC CTG GCC
tyr leu ala ala arg leu ser trp asn gln val asp gln val ile arg asn ala leu ala
400/101                            430/111
AGC CCC GGC AGC GGC GGC GAC CTG GGC GAA GCG ATC CGC GAG CAG CCG GAG CAG GCC CGT
ser pro gly ser gly gly asp leu gly glu ala ile arg glu gln pro glu gln ala arg
460/121                            490/131
CTG GCC CTG ACC CTG GCC GCC GCC GAG AGC GAG CGC TTC GTC CGG CAG GGC ACC GGC AAC
leu ala leu thr leu ala ala ala glu ser glu arg phe val arg gln gly thr gly asn
520/141                            550/151
GAC GAG GCC GGC GCG GCC AAG GCC GAC GTG GTG AGC CTG ACC TGC CCG GTC GCC GCC GGT
asp glu ala gly ala ala asn ala asp val val ser leu thr cys pro val ala ala gly
580/161                            610/171
GAA TGC GCG GGC CCG GCG GAC AGC GGC GAC GCC CTG CTG GAG CGC AAC TAT CCC ACT GGC
glu cys ala gly pro ala asp ser gly asp ala leu leu glu arg asn tyr pro thr gly
640/181                            670/191
GCG GAG TTC CTC GGC GAC GGC GGC GAC GTC AGC TTC AGC ACC CGC GGC ACG CAG AAC TGG
ala glu phe leu gly asp gly gly asp val ser phe ser thr arg gly thr gln asn trp
700/201                            730/211
ACG GTG GAG CGG CTG CTC CAG GCG CAC GCG GAA CTG GAG GAG CGC GGC TAT GTG TTC GTC
thr val glu arg leu leu gln ala his arg gln leu glu glu arg gly tyr val phe val
760/221                            790/231
GGC TAC CAC GGC ACC TTC CTC GAA GCG GCC CAA AGC ATC GTC TTC GGC GGG GTG CGC GCG
gly tyr his gly thr phe leu glu ala ala gln ser ile val phe gly gly val arg ala
820/241                            850/251
CGC AGC CAG GAC CTC GAC GCG ATC TGG CGC GGT TTC TAT ATC GCC GGC GAT CCG GCG CTG
arg ser gln asp leu asp ala ile trp arg gly phe tyr ile ala gly asp pro ala leu
880/261                            910/271
GCC TAC GGC TAC GCC CAG GAC CAG GAA CCC GAC GCA CGC GGC CGG ATC CGC AAC GGT GCC
ala tyr gly tyr ala gln asp gln glu pro asp ala arg gly arg ile arg asn gly ala
```

FIG.2A

940/281                                970/291
CTG CTG CGG GTC TAT GTG CCG CGC TCG AGC CTG CCG GGC TTC TAC CGC ACC AGC CTG ACC
leu leu arg val tyr val pro arg ser ser leu pro gly phe tyr arg thr ser leu thr
1000/301                               1030/311
CTG GCC GCG CCG GAG GCG GCG GGC GAG GTC GAA CGG CTG ATC GGC CAT CCG CTG CCG CTG
leu ala ala pro glu ala ala gly glu val glu arg leu ile gly his pro leu pro leu
1060/321                               1090/331
CGC CTG GAC GCC ATC ACC GGC CCC GAG GAG GAA GGC GGG CGC CTG GAG ACC ATT CTC GGC
arg leu asp ala ile thr gly pro glu glu glu gly gly arg leu glu thr ile leu gly
1120/341                               1150/351
TGG CCG CTG GCC GAG CGC ACC GTG GTG ATT CCC TCG GCG ATC CCC ACC GAC CCG CGC AAC
trp pro leu ala glu arg thr val val ile pro ser ala ile pro thr asp pro arg asn
1180/361                               1210/371
GTC GGC GGC GAC CTC GAC CCG TCC AGC ATC CCC GAC AAG GAA CAG GCG ATC AGC GCC CTG
val gly gly asp leu asp pro ser ser ile pro asp lys glu gln ala ile ser ala leu
1240/381                               1270/391
CCG GAC TAC GCC AGC CAG CCC GGC AAA CCG CCG CGC GAG GAC CTg aag TAA
pro asp tyr ala ser gln pro gly lys pro pro arg glu asp leu lys OCH

FIG.2B ic toxin, LGnRH-PE66M.
METHODS OF CANCER DIAGNOSIS USING A CHIMERIC TOXIN

INTRODUCTION

The present invention relates to methods for cancer diagnosis using a chimeric toxin. In particular, the invention relates to the use of a chimeric toxin composed of gonadotropin releasing hormone (GnRH) and Pseudomonas exotoxin A (PE) to detect a tumor-associated epitope expressed by human adenocarcinomas. Mutated GnRH-PE molecules that bind but do not kill tumor cells are exemplified.

BACKGROUND OF THE INVENTION

GnRH is a decapeptide produced by hypothalamic neurons and secreted into the hypophysioportal circulation via portal vessels. It is first synthesized as a larger precursor protein which is processed by proteolytic cleavage and amidation at its C-terminal glycine. GnRH stimulates gonadotroph cells in the anterior pituitary gland to release luteinizing hormone and follicle-stimulating hormone, thereby regulating the hypothalamic-pituitary gonadal control of human reproduction.

The involvement of GnRH has been implicated in certain carcinomas, and GnRH analogues have been used in the treatment of breast, prostatic, pancreatic, endometrial and ovarian cancers (Kadar et al., 1988, Prostate 12:229–307). The analogues suppressed tumor cell growth in vitro and in vivo. In addition, GnRH binding sites have been reported in certain solid tumors and in established cell lines (Emons et al., 1993, J. Clin. Endocrinol. Metab. 77:1458–1464), though preliminary results suggest that the GnRH receptor (GnRHR) involved might differ from the previously documented receptor (Kadar et al., 1992, Biochem. Biophs. Res. Comm. 189:289–295).

Although GnRH binding sites have been demonstrated in tumors, such tumors were derived mainly from hormone dependent tissues. Recently, Nechushtan et al. reported that certain hormone non-responsive tumors such as colon carcinomas, renal cell carcinomas and hepatocellular carcinomas were susceptible to killing by a chimeric toxin, GnRH-PE (J. Biol. Chem., 1997, 272:11597). GnRH caused the chimeric toxin to bind to GnRHR-expressing tumor cells, whereas PE mediated cell killing by inhibiting protein synthesis. However, prior to the present invention, it was not known whether the observed effects were due to the expression of a natural GnRHR by hormone non-responsive tumors or a new epitope recognized by GnRH-PE that was distinct from that bound by GnRH.

SUMMARY OF THE INVENTION

The present invention relates to methods for detecting a tumor cell using a GnRH-PE chimeric toxin, and GnRH-PE chimeric toxins that bind but do not kill tumor cells. In particular, it relates to the use of a GnRH-PE chimeric toxin to detect an epitope expressed by adenocarcinomas. For the practice of the invention, it is preferred that the GnRH-PE is modified to reduce its cytotoxic activities without altering its binding specificity to tumor cells. Such molecules are particularly useful for the detection of tumor cells in a biological specimen and in a human subject who has cancer.

The invention is based, in part, on Applicants' discovery that two mutated recombinant chimeric toxins composed of GnRH and PE, referred to as LGnRH-PE40M and LGnRH-PE66M, bind to tumor cells without killing them. Since these chimeric toxins do not bind granulosa tumor cells which express natural GnRHR recognized by GnRH, the chimeric toxins of the invention recognize a new tumor-associated epitope expressed by adenocarcinomas.

BRIEF DESCRIPTION OF THE DRAWINGS

FIGS. 1A, 1B and 1C. Nucleotide sequence (SEQ ID NO:1) and amino acid sequence (SEQ ID NO:2) of LGnRH-PE66. Amino acid residue #575 identified within a square is deleted in a mutated chimeric toxin, LGnRH-PE66M.

FIG. 2. Nucleotide sequence (SEQ ID NO:3) and amino acid sequence (SEQ ID NO:4) of LGnRH-PE40. Amino acid residue #336 identified within a square is deleted in a mutated chimeric toxin, LGnRH-PE40M.

DETAILED DESCRIPTION OF THE INVENTION

Production of GnRH-PE Chimeric Toxins

Figure 3:
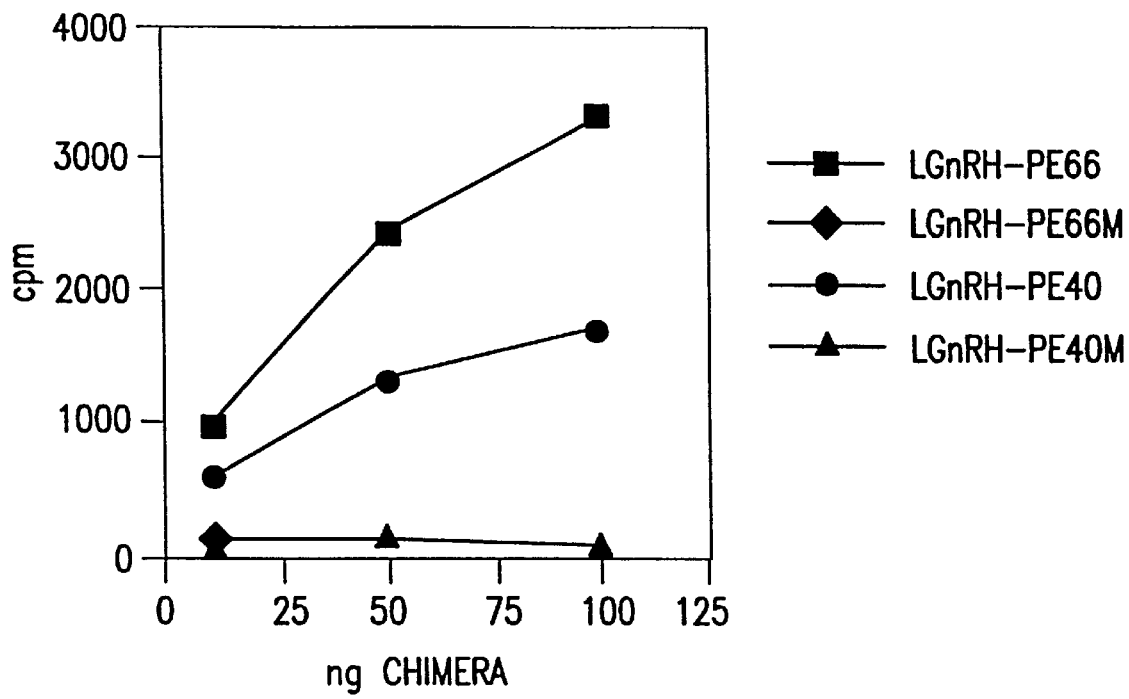
FIG. 3. Mutated GnRH-PE chimeric toxins, LGnRH-PE40M and LGnRH-PE66M, did not exhibit ADP-ribosylation activities.

While the GnRH-PE chimeric toxins of the present invention may be produced by chemical synthetic methods or by chemical linkage between the two moieties, it is preferred that they are produced by fusion of a coding sequence for GnRH and a coding sequence for PE under the control of a regulatory sequence which directs the expression of the fusion polynucleotide in an appropriate host cell (Nechushtan et al., 1997, J. Biol. Chem. 272:11597). The fusion of two coding sequences can be achieved by methods well known in the art of molecular biology. The PE coding sequence suitable for use in the present invention, includes but is not limited to, full length PE, partial fragments of PE such as domains II and/or III of PE, mutated PE in which amino acid residues in domain I have been altered to reduce non-specific cytotoxicity and mutated PE which has minimal cytotoxic activities (U.S. Pat. No. 4,892,827, Lorberboum-Galski et al., 1990, J. Biol. Chem. 265:16311).

It is preferred that a fusion polynucleotide contain only the AUG translation initiation codon at the 5' end of the first coding sequence without the initiation codon of the second coding sequence to avoid the production of two encoded products. In addition, a leader sequence may be placed at the 5' end of the polynucleotide in order to target the expressed product to a specific site or compartment within a host cell to facilitate secretion or subsequent purification after gene expression. The two coding sequences can be fused directly without any linker or by using a flexible polylinker composed of the pentamer Gly-Gly-Gly-Gly-Ser (SEQ ID NO:5) repeated 1 to 3 times. Such linker has been used in constructing single chain antibodies (scFv) by being inserted between $V_H$ and $V_L$ (Bird et al., 1988, Science 242:423–426; Huston et al., 1988, Proc. Natl. Acad. Sci. U.S.A. 85:5979–5883). The linker is designed to enable the correct interaction between two beta-sheets forming the variable region of the single chain antibody. Other linkers which may be used include Glu-Gly-Lys-Ser-Ser-Gly-Ser-Gly-Ser-Glu-Ser-Lys-Val-Asp (SEQ ID NO:6) (Chaudhary et al., 1990, Proc. Natl. Acad. Sci. U.S.A. 87:1066–1070) and Lys-Glu-Ser-Gly-Ser-Val-Ser-Ser-Glu-Gln-Leu-Ala-Gln-Phe-Arg-Ser-Leu-Asp (SEQ ID NO:7) (Bird et al., 1988, Science 242:423–426).

Expression of GnRH-PE Chimeric Toxins

A polynucleotide which encodes a GnRH-PE chimeric toxin, mutant polypeptides, biologically active fragments of chimeric protein, or functional equivalents thereof, may be used to generate recombinant DNA molecules that direct the expression of the chimeric toxin, mutant polypeptides, peptide fragments, or a functional equivalent thereof, in appropriate host cells. Due to the inherent degeneracy of the genetic code, other DNA sequences which encode substantially the same or a functionally equivalent amino acid sequence, may be used in the practice of the invention for the cloning and expression of the chimeric toxin.

Altered DNA sequences which may be used in accordance with the invention include deletions, additions or substitutions of different nucleotide residues resulting in a sequence that encodes the same or a functionally equivalent fusion gene product. The gene product itself may contain deletions, additions or substitutions of amino acid residues within a chimeric sequence, which result in a silent change thus producing a functionally equivalent chimeric protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The DNA sequences of the invention may be engineered in order to alter a chimeric coding sequence for a variety of ends, including but not limited to, alterations which modify processing and expression of the gene product. For example, mutations may be introduced using techniques which are well known in the art, e.g., site-directed mutagenesis, to insert new restriction sites, to reduce cytotoxicities, etc.

In an alternate embodiment of the invention, the coding sequence of the GnRH-PE chimeric toxin could be synthesized in whole or in part, using chemical methods well known in the art. See, for example, Caruthers et al., 1980, *Nuc. Acids Res. Symp. Ser.* 7:215–233; Crea and Horn, 180, *Nuc. Acids Res.* 9(10):2331; Matteucci and Caruthers, 1980, *Tetrahedron Letter* 21:719; and Chow and Kempe, 1981, *Nuc. Acids Res.* 9(12):2807–2817. In addition, GnRH decapeptide and specific domains of PE can be synthesized by solid phase techniques, cleaved from the resin, and purified by preparative high performance liquid chromatography followed by chemical linkage to form a chimeric toxin (e.g., see Creighton, 1983, *Proteins Structures And Molecular Principles*, W.H. Freeman and Co., N.Y. pp. 50–60). The composition of the synthetic peptides may be confirmed by amino acid analysis or sequencing (e.g., the Edman degradation procedure; see Creighton, 1983, *Proteins, Structures and Molecular Principles*, W.H. Freeman and Co., N.Y., pp. 34–49). Alternatively, the GnRH and PE produced by synthetic or recombinant methods may be conjugated by chemical linkers according to methods well known in the art (Brinkmann and Pastan, 1994, *Biochemica et Biophysica Acta* 1198:27–45).

In order to express a biologically active GnRH-PE chimeric toxin, the nucleotide sequence coding for a chimeric toxin, or a functional equivalent, is inserted into an appropriate expression vector, i.e., a vector which contains the necessary elements for the transcription and translation of the inserted coding sequence. The chimeric toxin as well as host cells or cell lines transfected or transformed with recombinant chimeric expression vectors can be used for a variety of purposes. These include but are not limited to generating antibodies (i.e., monoclonal or polyclonal) that bind to epitopes of the proteins to facilitate their purification.

Methods which are well known to those skilled in the art can be used to construct expression vectors containing the GnRH-PE chimeric toxin coding sequence and appropriate transcriptional/translational control signals. These methods include in vitro recombinant DNA techniques, synthetic techniques and in vivo recombination/genetic recombination. See, for example, the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the GnRH-PE chimeric protein coding sequence. These include but are not limited to microorganisms such as bacteria transformed with recombinant bacteriophage DNA, plasmid DNA or cosmid DNA expression vectors containing the chimeric toxin coding sequence; yeast transformed with recombinant yeast expression vectors containing the chimeric toxin coding sequence; insect cell systems infected with recombinant virus expression vectors (e.g., baculovirus) containing the chimeric toxin coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the chimeric toxin coding sequence; or animal cell systems. It should be noted that since PE normally kills mammalian cells, it is preferred that the chimeric toxins of the invention be expressed in prokaryotic or lower eukaryotic cells. Section 6 illustrates that GnRH-PE chimeric toxins can be efficiently expressed in *E. coli*. However, since the mutated GnRH-PE chimeric toxins in Section 6, infra, do not exhibit cytotoxic activities towards human cells, they may be expressed in eukaryotic cells as well.

The expression elements of each system vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage X, plac, ptrp, ptac (ptrp-lac hybrid promoter; cytomegalovirus promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the chimeric DNA, SV40-, BPV- and EBV-based vectors may be used with an appropriate selectable marker.

In bacterial systems a number of expression vectors may be advantageously selected depending upon the use intended for the chimeric toxin expressed. For example, when large quantities of chimeric toxin are to be produced, vectors which direct the expression of high levels of protein products that are readily purified may be desirable. Such vectors include but are not limited to the pHL906 vector (Fishman et al., 1994, Biochem. 33:6235–6243), the *E. coli* expression vector pUR278 (Ruther et al., 1983, *EMBO J.* 2:1791), in which the chimeric protein coding sequence may be ligated into the vector in frame with the lacZ coding region so that a hybrid lacZ protein is produced; pIN vectors (Inouye & Inouye, 1985, Nucleic acids Res. 13:3101–3109; Van Heeke & Schuster, 1989, J. Biol. Chem. 264:5503–5509); and the like.

An alternative expression system which could be used to express chimeric toxin is an insect system. In one such system, *Autographa californica* nuclear polyhidrosis virus (AcNPV) is used as a vector to express foreign genes. The virus grows in *Spodoptera frugiperda* cells. The chimeric toxin coding sequence may be cloned into non-essential regions (for example the polyhedrin gene) of the virus and placed under control of an AcNPV promoter (for example the polyhedrin promoter). Successful insertion of the chimeric protein coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Viol. 46:584; Smith, U.S. Pat. No. 4,215,051).

Specific initiation signals may also be required for efficient translation of the inserted chimeric toxin coding sequence. These signals include the ATG initiation codon and adjacent sequences. In cases where the entire chimeric gene, including its own initiation codon and adjacent sequences, is inserted into the appropriate expression vector, no additional translational control signals may be needed. However, in cases where the chimeric toxin coding sequence does not include its own initiation codon, exogenous translational control signals, including the ATG initiation codon, must be provided. Furthermore, the initiation codon must be in phase with the reading frame of the chimeric protein coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the chimeric toxin. To this end, eukaryotic host cells which possess the cellular machinery for proper processing of the primary transcript, glycosylation, and phosphorylation of the chimeric protein may be used. Such mammalian host cells include but are not limited to CHO, VERO, BHK, HeLa, COS, MDCK, 293, WI38, and the like.

For long-term, high-yield production of recombinant chimeric toxins, stable expression is preferred. For example, bacterial host cells or eukaryotic cell lines which stably express the chimeric toxins may be engineered. Rather than using expression vectors which contain viral origins of replication, host cells can be transformed with a chimeric coding sequence controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. U.S.A. 48:2026), and adenine phosphoribosyltransferase (Lowy et al., 1980, Cell 22:817) genes can be employed in $tk^-$, $hgprt^-$ or $aprt^-$ cells, respectively. Also, antimetabolite resistance can be used as the basis of selection for dhfr, which confers resistance to methotrexate (Wigler et al., 1980, Natl. Acad. Sci. U.S.A. 77:3567; O'Hare et al., 1981, Proc. Natl. Acad. Sci. U.S.A. 78:1527); gpt, which confers resistance to mycophenolic acid (Mulligan & Berg, 1981, Proc. Natl. Acad. Sci. U.S.A. 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes. Additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. U.S.A. 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Protein Purification

The GnRH-PE chimeric toxins of the invention can be purified by art-known techniques such as high performance liquid chromatography, ion exchange chromatography, gel electrophoresis, affinity chromatography and the like. The actual conditions used to purify each protein will depend, in part, on factors such as net charge, hydrophobicity, hydrophilicity, etc., and will be apparent to those having skill in the art.

For affinity chromatography purification, any antibody which specifically binds GnRH, PE or a conformational epitope created by the fusion of GnRH and PE may be used. For the production of antibodies, various host animals, including but not limited to rabbits, mice, rats, etc., may be immunized by injection with GnRH-PE chimeric toxin or a portion thereof. The protein may be attached to a suitable carrier, such as bovine serum albumin (BSA), by means of a side chain functional group or linkers attached to a side chain functional group. Various adjuvants may be used to increase the immunological response, depending on the host species, including but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum.*

Monoclonal antibodies to GnRH-PE may be prepared using any technique which provides for the production of antibody molecules by continuous cell lines in culture. These include but are not limited to the hybridoma technique originally described by Koehler and Milstein (1975, *Nature* 256:495–497). In addition, techniques developed for the production of "chimeric antibodies" (Morrison et al., 1984, *Proc. Natl. Acad. Sci. U.S.A.* 81:6851–6855; Neuberger et al., 1984, *Nature* 312:604–608; Takeda et al., 1985, *Nature* 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce GnRH-PE-specific single chain antibodies for protein purification and detection.

Cancer Diagnosis Using GnRH-PE Chimeric Toxins

The GnRH-PE chimeric toxins of the invention may be used to detect human tumors in vitro and in vivo. It is preferred that such toxins be mutated to abrogate their cytotoxic properties without affecting their binding specificity for tumor cells. Two examples of such GnRH-PE are illustrated in Section 6, infra. The GnRH-PE chimeric toxins of the invention may be used to detect an epitope expressed by a wide variety of human adenocarcinomas, including but not limited to, colon adenocarcinoma, breast adenocarcinoma, lung adenocarcinoma, ovarian adenocarcinoma, endometrial adenocarcinoma, kidney adenocarcinoma, liver adenocarcinoma, prostate adenocarcinoma, stomach adenocarcinoma, cervical adenocarcinoma, gall bladder adenocarcinoma and pancreatic adenocarcinoma. The chimeric toxins of the invention are particularly useful in differentiating adenocarcinomas from non-adenocarcinomas and normal cells that express the natural GnRHR.

In Vitro Diagnostic Applications

The GnRH-PE chimeric toxins of the present invention can be used to detect cancer cells in a biological specimen such as histological and cytological specimens, and, in particular, to distinguish malignant tumors from normal tissues and non-malignant tumors for determination of surgical margin and an improved histological characterization of poorly differentiated tumors. Tissue specimens may be stained by the chimeric toxins and their binding detected by a secondary antibody specific for a portion of the chimeric toxin. The secondary antibody is conjugated to a detectable label such as a radioisotope, an enzyme such as peroxidase and alkaline phosphatase, an ultrasonic probe, a nuclear magnetic resonance (NMR) probe, and the like.

In addition, immunofluorescence techniques can use GnRH-PE to examine human tissue, cell and bodily fluid specimens. In a typical protocol, slides containing cryostat sections of frozen, unfixed tissue biopsy samples or cytological smears are air dried, formalin or acetone fixed, and incubated with the GnRH-PE in a humidified chamber at room temperature.

The slides are then washed and further incubated with a preparation of a secondary antibody directed against GnRH-PE. The secondary antibody is tagged with a compound such as rhodamine, phycoerythrin or fluorescein isothiocyanate, that fluoresces at a particular wavelength. The staining pattern and intensities within the sample are then determined by fluorescent light microscopy and optionally photographically recorded.

In another embodiment, computer enhanced fluorescence image analysis or flow cytometry can be used to examine tissue specimens or exfoliated cells, i.e., single cell preparations from aspiration biopsies of tumors using GnRH-PE. The GnRH-PE chimeric toxins of the invention are particularly useful in quantitation of live tumor cells, i.e., single cell preparations from aspiration biopsies of adenocarcinomas by computer enhanced fluorescence image analyzer or with a flow cytometer. The percent GnRH-PE-bound cell population, alone or in conjunction with determination of the DNA ploidy of these cells, may, additionally, provide very useful prognostic information by providing an early indicator of disease progression.

The use of GnRH-PE can be extended to the screening of human biological fluids for the presence of the specific antigenic determinants recognized. In vitro immunoserological evaluation of biological fluids withdrawn from patients thereby permits non-invasive diagnosis of cancers. By way of illustration, human bodily fluids such as whole blood, pleural effusion fluid, cerebral spinal fluid, synovial fluid, prostatic fluid, seminal fluid or urine can be taken from a patient and assayed for the specific epitope, either as released antigen or membrane-bound on cells in the sample fluid, using GnRH-PE in standard radioimmunoassays or enzyme-linked immunoassays, competitive binding enzyme-linked immunoassays, dot blot or Western blot, or other assays known in the art.

Kits containing GnRH-PE can be prepared for in vitro diagnosis, prognosis and/or monitoring adenocarcinomas by the immunohistological, immunocytological and immunoserological methods described above. The components of the kits can be packaged either in aqueous medium or in lyophilized form. When the GnRH-PE is used in the kits in the form of conjugates in which a label moiety is attached, such as an enzyme or a radioactive metal ion, the components of such conjugates can be supplied either in fully conjugated form, in the form of intermediates or as separate moieties to be conjugated by the user of the kit.

A kit may comprise a carrier being compartmentalized to receive in close confinement therein one or more container means or series of container means such as test tubes, vials, flasks, bottles, syringes, or the like. A first of said container means or series of container means may contain GnRH-PE. A second container means or series of container means may contain a label or linker-label intermediate capable of binding to GnRH-PE.

In Vivo Diagnostic Applications

GnRH-PE chimeric toxins are also useful for targeting adenocarcinoma cells in vivo. They can be used for tumor localization in the detection and monitoring of primary tumors as well as metastases, especially lymph nodes. Primary evaluation of the extent of tumor spread may influence the choice of therapeutic modalities. Continued monitoring of residual tumors may also contribute to better surveillance and early initiation of salvage therapy. Tagged GnRH-PE may also be used intraoperatively for better debulking of a tumor, and minimizes normal tissue destruction such as lymph nodes. For these in vivo applications, it is preferred that highly purified GnRH-PE be used.

For in vivo detection and/or monitoring of adenocarcinomas, the purified GnRH-PE can be covalently attached, either directly or via a linker, to a compound which serves as a reporter group to permit imaging of specific tissues or organs following administration and localization of the conjugates or complexes. A variety of different types of substances can serve as the reporter group, including such as radiopaque dyes, radioactive metal and non-metal isotopes, fluorogenic compounds, fluorescent compounds, positron emitting isotopes, non-paramagnetic metals, etc.

Kits for use with such in vivo tumor localization methods containing GnRH-PE (or fragments thereof) conjugated to any of the above types of substances can be prepared. The components of the kits can be packaged either in aqueous medium or in lyophilized form. When the chimeric toxins are used in the kits in the form of conjugates in which a label is attached, the components of such conjugates can be supplied either in fully conjugated form, in the form of intermediates or as separate moieties to be conjugated by the user of the kit.

EXAMPLE

Mutated GnRH-PE Chimeric Toxins Bound but did not Kill Tumor Cells

Materials and Methods

Construction of GnRH-PE Chimeric Toxins

A plasmid vector carrying a full length PE gene (pJY3A1136-1,3) (Chaudhary et al., 1990, J. Biol. Chem. 265:16306–16310; Neshushtan et al., 1997, J. Biol. Chem. 272:11597) was cut with NdeI and HindIII. A 36 base pair (bp) synthetic oligomer flanked by NdeI (5' end) and HindIII (3' end) restriction sites was ligated to the vector. This oligomer insert contained a GnRH coding sequence in which the encoded amino acid at residue #6 was tryptophan instead of glycine. In addition, a sequence encoding a linker Gly-Gly-Gly-Gly-Ser (SEQ ID NO:5) repeated twice was placed between the GnRH coding sequence and the PE coding sequence. The resultant plasmid encoded a chimeric toxin, LGnRH-PE66, and it was confirmed by restriction endonuclease digestion and DNA sequence analysis (FIGS. 1A and 1B).

In order to produce a second chimeric toxin, LGnRH-PE40, the plasmid vector encoding LGnRH-PE66 was digested with NdeI and BamHI and ligated to a NdeI-BamHI 750 bp fragment obtained from the plasmid PHL-906 (Fishman et al., 1994, Biochemistry 33:6235–6243) along with the 36 bp synthetic oligomer consisting of the GnRH coding sequence with tryptophan replacing glycine at the sixth amino acid position. A sequence encoding the above linker was again placed between the GnRH coding sequence and the PE coding sequence. The resultant plasmid encoded a chimeric toxin, LGnRH-PE40, and it was confirmed by restriction endonuclease digestion and DNA sequence analysis (FIG. 2). The toxin encoded by this plasmid consisted of domains II and III of the full-length PE.

Generation of Mutated GnRH-PE Chimeric Toxins

In order to construct GnRH-PE chimeric toxins that were not cytotoxic to human cells, the region in the two aforementioned plasmids that encoded 122 amino acids at the C-terminal end of PE of LGnRH-PE66 and LGnRH-PE40 was excised with BamHI and EcoRI and replaced with a corresponding fragment which contained a deletion of a single codon encoding the amino acid at position 553 of the native PE molecule (FIGS. 1A, 1B and 2) (Fishman et al., 1997, Eur. J. Immunol. 27:486; Lukoc et al., 1988, Infect. Immun. 56:3095). The mutated chimeric toxins are referred to as LGnRH-PE66M and LGnRH-PE40M, respectively.

Expression of GnRH-PE Chimeric Toxins

The plasmids, pVM1 and pVM2, encoding the mutated GnRH-PE chimeric toxins, LGnRH-PE66M and LGnRH-PE40M, respectively, were expressed in E. coli strain BL21 (XDE3). The plasmids that encoded LGnRH-PE40 and LGnRH-PE66 were also expressed in the same bacteria. The plasmids were transferred into E. coli and the cells were grown in medium containing ampicillin. After reaching an $A_{600}$ value of 1.5–1.7, the cultures were induced at 37° C. with 1 mM isopropyl-1-thio-β-D-galactopyranoside. The cells were collected by centrifugation and the pellet was stored at −70° C. for several hours.

A pellet of expressing cells was suspended in lysis buffer (50 mM Tris-HCl at pH 8.0, 1 mM EDTA containing 0.2 mg/ml lysosyme), sonicated (three 30 second bursts) and centrifuged at 30,000×g for 30 min. The supernatant (soluble fraction) was removed and kept for analysis. The pellet (insoluble fraction) was denatured in extraction buffer (6 M guanidinium-HCl, 0.1 M Tris-HCl, pH 8.6, 1 mM EDTA, 0.05 M NaCl, and 10 mM dithiothreitol) and stirred for 30 min at 4° C. The suspension was cleared by centrifugation at 30000×g for 15 min and the pellet discarded. The supernatant was then dialyzed against 0.1 M Tris-HCl pH 8.0, 1 mM EDTA, 0.25 mM NaCl, and 0.25 mM L-arginine for 16 hours. The dialyzate was centrifuged at 15000×g for 15 min and the resulting supernatant (refolding fraction) was used as a source of the GnRH-PE chimeric toxins.

Analysis of the fraction by SDS/PAGE revealed a major band corresponding to the chimeric toxin. Immunoblotting with polyclonal antibodies against PE confirmed the production of GnRH-PE chimeric toxins.

Purification of Recombinant GnRH-PE Chimeric Toxins

The refolded protein fractions were diluted with TE20 buffer (20 mM Tris, pH 8.0, 1 mM EDTA). DEAE Sepharose (Pharmacia, Sweden) was added and stirred for half an hour at 4° C. before being packed into a column. Washing of the column was done with 80 mM NaCl or 50 mM Nacl in TE20 buffer. Elution of protein was performed with the linear gradient of 2×200 ml of 0.08–0.35 M NaCl in TE20 (20 mM Tris pH 8.0, 1 mM EDTA) buffer. The peak fractions were pooled, dialyzed against phosphate saline buffer and kept in aliquots at −20° C.

Results

A recombinant GnRH-PE chimeric toxin, LGnRH-PE66, was produced by fusion of a GnRH coding sequence and a PE coding sequence with the insertion of a linker between the two moieties. A second GnRH-PE chimeric toxin, LGnRH-PE40, was produced in a similar manner except that only domains II and III of PE was encoded by the toxin coding sequence. In addition, the coding sequences of these two chimeric toxins were mutated to result in a single amino acid deletion in the PE portion. The mutated chimeric toxins were also expressed as recombinant proteins.

The four GnRH-PE chimeric toxins were purified from E. coli lysates and refolded. Since PE kills eukaryotic cells by inactivating elongation factor 2 through ADP-ribosylation during protein synthesis, the four forms of GnRH-PE chimeric toxins were tested in a cell free assay for their enzymatic activities in ADP-ribosylation (Chung and Collier, 1977, J. Infect. Immun. 16:832–841). While the two non-mutated GnRH-PE chimeric toxins, LGnRH-PE40 and LGnRH-PE66, exhibited ADP-ribosylation activities, the mutated chimeric toxins, LGnRH-PE40M and LGnRH-PE66M, were completely inactive in the same assay (FIG. 3). Thus, a single amino acid substitution in PE abrogated the enzymatic activities of the chimeric toxins.

Figure 4:
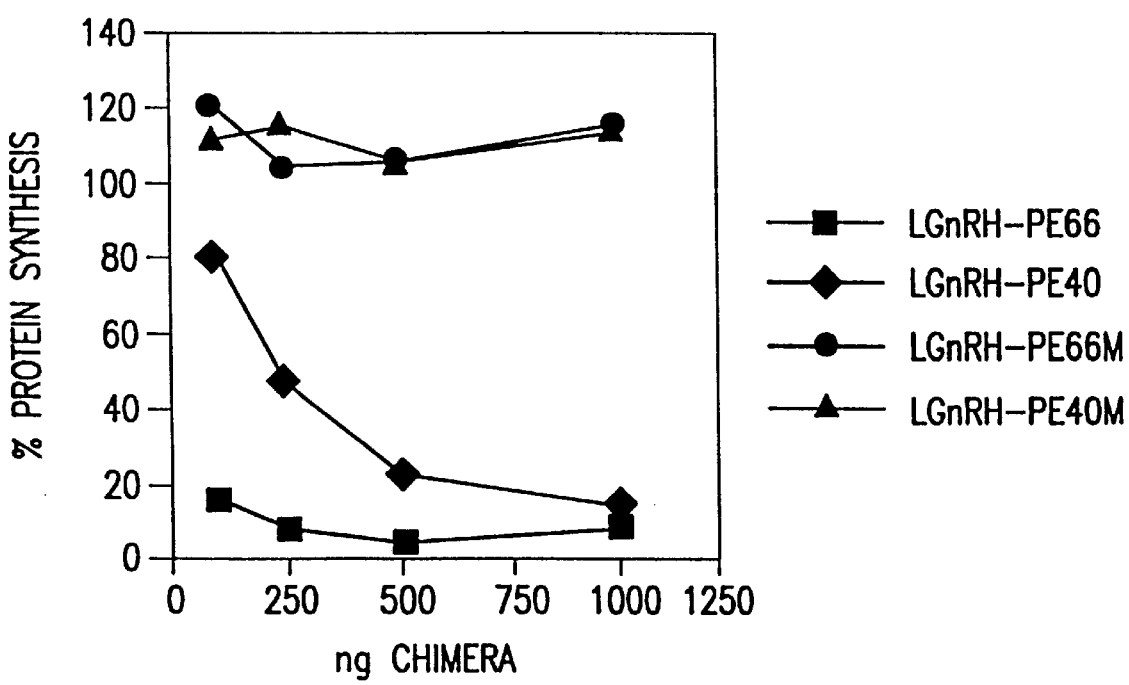
FIG. 4. Mutated GnRH-PE chimeric toxins, LGnRH-PE40M and LGnRH-PE66M, did not inhibit protein synthesis in 293 renal carcinoma cells, while the non-mutated chimeric toxins showed cytotoxic activities. Inhibition of protein synthesis is used as an indication of cytotoxicity.

In addition, all four GnRH-PE chimeric toxins were tested for their ability to kill 293 renal adenocarcinoma cells. It was shown that only the non-mutated chimeric toxins showed dose-dependent inhibition of protein synthesis in the target cells (FIG. 4). However, when the chimeric toxins were incubated with the same target cells and their binding was detected by a labeled anti-PE antibody and FACS analysis, all four toxins were able to bind renal carcinoma cells with no binding to control T24A bladder carcinoma cells. Therefore, while the mutated GnRH-PE chimeric toxins were not able to kill target cells, they retained the ability to bind to tumor cells. Such non-cytotoxic chimeric toxins are particularly useful for use in cancer diagnosis in vitro and in vivo.

Figure 5:
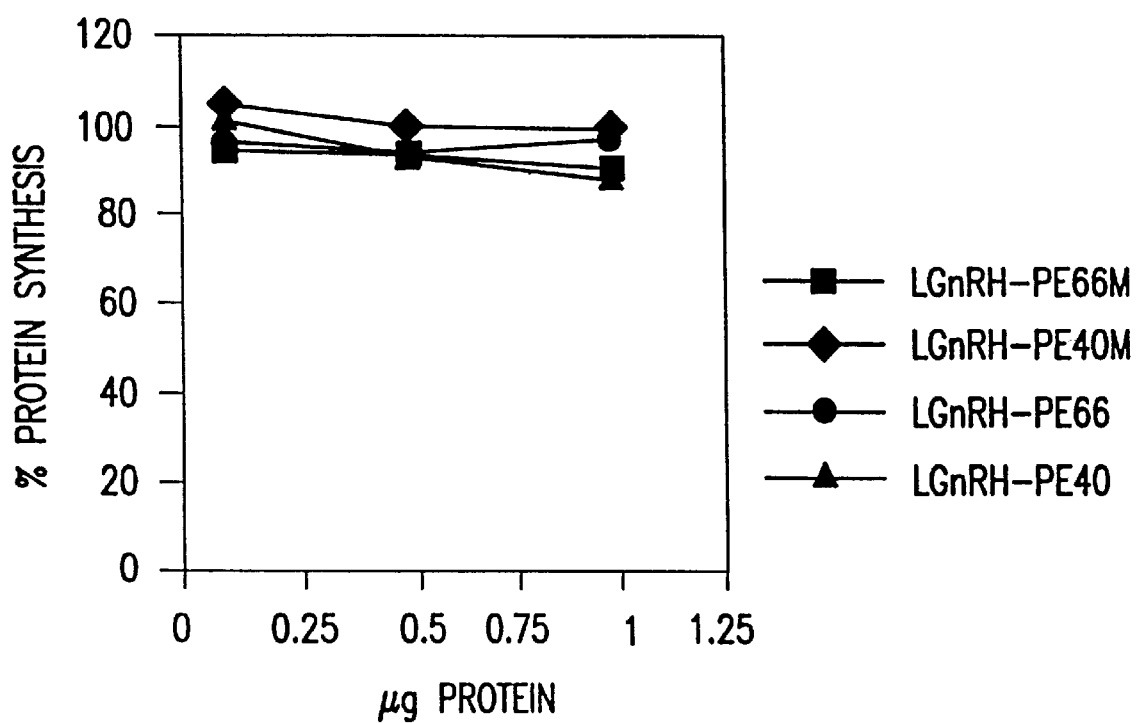
FIG. 5. GnRH-PE chimeric toxins did not inhibit protein synthesis of primary cultures of granulosa tumor cells which expressed natural GnRHR.

Primary granulosa tumor cells were obtained and shown to express GnRHR by PCR using primers corresponding to specific portions of the GnRHR. The PCR product in granulosa cells was the same size as that obtained from pituitary cells which expressed natural GnRHR. In contrast, GnRHR-negative cells such as normal human lymphocytes did not produce a detectable PCR product. Notwithstanding their expression of natural GnRHR, the granulosa cells were not susceptible to killing by any of the four GnRH-PE chimeric toxins, indicating that the chimeric toxins bind to a new epitope expressed by adenocarcinoma cells that is distinct from that bound by GnRH itself (FIG. 5).

The present invention is not to be limited in scope by the exemplified embodiments which are intended as illustrations of single aspects of the invention and any sequences which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for detecting a tumor cell in a biological specimen, comprising contacting the biological specimen with a chimeric toxin with comprises gonadotropin releasing hormone and Pseudomonas exotoxin A, and detecting chimeric toxin-bound cells in the specimen.

2. The method of claim 1 in which biological specimen contains adenocarcinoma cells.

3. The method of claim 2 in which the adenocarcinoma cells are selected from a group consisting of colon adenocarcinoma, breast adenocarcinoma, lung adenocarcinoma, ovarian adenocarcinoma, endometrial adenocarcinoma, kidney adenocarcinoma, liver adenocarcinoma, prostate adenocarcinoma, stomach adenocarcinoma, cervical adenocarcinoma, gall bladder adenocarcinoma and pancreatic adenocarcinoma.

4. The method of claim 1 in which the Pseudomonas exotoxin is a full-length toxin.

5. The method of claim 1 in which the Pseudomonas exotoxin contains only domains II and III of a full-length toxin.

6. The method of claim 1 in which the chimeric toxin comprises the amino acid sequence as shown in SEQ ID NO:2.

7. The method of claim 6 in which the chimeric toxin is encoded by a polynucleotide which comprises the nucleotide sequence as shown in SEQ ID NO:1.

8. The method of claim 1 in which the chimeric toxin comprises the amino acid sequence of SEQ ID NO:4.

9. The method of claim 8 in which the chimeric toxin is encoded by a polynucleotide which comprises the nucleotide sequence as shown in SEQ ID NO:3.

10. The method of claim 1 in which the Pseudomonas exotoxin is altered to be non-cytotoxic.

11. The method of claim 10 in which the Pseudomonas exotoxin is altered to be non-cytotoxic by deleting an amino acid residue.

12. The method of claim 1 in which the chimeric toxin comprises the amino acid sequence as shown in SEQ ID NO:2 wherein amino acid residue #575 is deleted.

13. The method of claim 12 in which the chimeric toxin is encoded by a polynucleotide which comprises the nucleotide sequence as shown as SEQ ID NO:1 wherein nucleotides #1822–1824 are deleted.

14. The method of claim 1 in which the chimeric toxin comprises the amino acid sequence as shown in SEQ ID NO:4 wherein amino acid residue #336 is deleted.

15. The method of claim 14 in which the chimeric toxin is encoded by a polynucleotide which comprises the nucleotide sequence as shown in SEQ ID NO:3 wherein nucleotides #1105–1107 are deleted.

16. The method of claim 1 in which the chimeric toxin is conjugated to a detectable label.

17. The method of claim 16 in which the detectable label is a radioisotope, a fluorescent dye, an enzyme, an ultrasonic probe or a NMR probe.

18. The method of claim 1 in which the biological specimen is a biopsy specimen.

19. The method of claim 1 in which the biological specimen is a bodily fluid.

20. The method of claim 19 in which the bodily fluid is whole blood.

21. The method of claim 19 in which the bodily fluid is pleural effusion fluid.

22. The method of claim 19 in which the bodily fluid is urine.

23. A method of detecting a tumor cell in a human subject, comprising administering to the subject a chimeric toxin which comprises gonadotropin releasing hormone and Pseudomonas exotoxin A, and detecting chimeric toxin-bound cells in the subject.

24. The method of claim 23 in which the subject has adenocarcinoma.

25. The method of claim 24 in which the adenocarcinoma is selected from a group consisting of colon adenocarcinoma, breast adenocarcinoma, lung adenocarcinoma, overian adenocarcinoma, endometrial adenocarcinoma, kidney adenocarcinoma, liver adenocarcinoma, prostate adenocarcinoma, stomach adenocarcinoma, cervical adenocarcinoma, gall bladder adenocarcinoma and pancreatic adenocarcinoma.

26. The method of claim 23 in which the Pseudomonas exotoxin is altered to be non-cytotoxic.

27. The method of claim 26 in which the Pseudomonas exotoxin is altered to be non-cytotoxic by deleting an amino acid residue.

28. The method of claim 23 in which the chimeric toxin comprises the amino acid sequence as shown in SEQ ID NO:2 wherein amino acid residue #575 is deleted.

29. The method of claim 28 in which the chimeric toxin is encoded by a polynucleotide which comprises the nucleotide sequence as shown in SEQ ID NO:1 wherein nucleotides #1822–1824 are deleted.

30. The method of claim 23 in which the chimeric toxin comprises the amino acid sequence as shown in SEQ ID NO:4 wherein amino acid residue #336 is deleted.

31. The method of claim 30 in which the chimeric toxin is encoded by a polynucleotide which comprises the nucleotide sequence as shown in SEQ ID NO:3 wherein nucleotides #1105–1107 are deleted.

32. The method of claim 23 in which the chimeric toxin is conjugated to a detectable label.

33. The method of claim 32 in which the detectable label is a radioisotope, a fluorescent dye, an enzyme, an ultrasonic probe or a NMR probe.

34. A chimeric toxin comprising gonadotropin releasing hormone and Pseudomonas exotoxin A which comprises the amino acid sequence as shown in SEQ ID NO:2 wherein the amino acid residue #575 is deleted.

35. The chimeric toxin of claim 34 which is encoded by a polynucleotide which comprises the nucleotide sequence as shown in SEQ ID NO:1 wherein nucleotides #1822–1824 are deleted.

36. A chimeric toxin comprising gonadotropin releasing hormone and Pseudomonas exotoxin A which comprises the amino acid sequence as shown in SEQ ID NO:4 wherein the amino acid residue #336 is deleted.

37. The chimeric toxin of claim 36 which is encoded by a polynucleotide which comprises the nucleotide sequence as shown in SEQ ID NO:3 wherein nucleotides #1105–1107 are deleted.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 1908 base pairs
      (B) TYPE: nucleic acid
      (C) STRANDEDNESS: single
      (D) TOPOLOGY: linear (ix) FEATURE:
      (A) NAME/KEY: Coding Sequence
      (B) LOCATION: 1...1905
      (D) OTHER INFORMATION:

(xi) SEQUENCE DESCRIPTION: SEQ ID NO:1:

```
ATG GAG CAC TGG TCC TAT TGG CTG CGC CCT GGA GAA GCT GGA GGA GGA        48
Met Glu His Trp Ser Tyr Trp Leu Arg Pro Gly Glu Ala Gly Gly Gly
 1               5                  10                  15

GGA TCC GGA GGA GGA GGA TCC GGT CAA GCT TTC GAC CTC TGG AAC GAA        96
Gly Ser Gly Gly Gly Gly Ser Gly Gln Ala Phe Asp Leu Trp Asn Glu
            20                  25                  30

TGC GCC AAA GCC TGC GTG CTC GAC CTC AAG GAC GGC GTG CGT TCC AGC       144
Cys Ala Lys Ala Cys Val Leu Asp Leu Lys Asp Gly Val Arg Ser Ser
        35                  40                  45

CGC ATG AGC GTC GAC CCG GCC ATC GCC GAC ACC AAC GGC CAG GGC GTG       192
Arg Met Ser Val Asp Pro Ala Ile Ala Asp Thr Asn Gly Gln Gly Val
    50                  55                  60

CTG CAC TAC TCC ATG GTC CTG GAG GGC GGC AAC GAC GCG CTC GAG CTG       240
Leu His Tyr Ser Met Val Leu Glu Gly Gly Asn Asp Ala Leu Glu Leu
65                  70                  75                  80

GCC ATC GAC AAC GCC CTC AGC ATC ACC AGC GAC GGC CTG ACC ATC CGC       288
Ala Ile Asp Asn Ala Leu Ser Ile Thr Ser Asp Gly Leu Thr Ile Arg
                85                  90                  95

CTC GAA GGC GGC GTC GAG CCG AAC AAG CCG CTC CGC TAC AGC TAC ACG       336
Leu Glu Gly Gly Val Glu Pro Asn Lys Pro Leu Arg Tyr Ser Tyr Thr
            100                 105                 110

CGC CAG GCG CGC GGC AGG TGG TCG CTG AAC TGG CTG GTA CCG ATC GGC       384
Arg Gln Ala Arg Gly Arg Trp Ser Leu Asn Trp Leu Val Pro Ile Gly
        115                 120                 125
```

```
                                               -continued

CAC GAG AAG CCC TCG AAC ATC AAG GTG TTC ATC CAC GAA CTG AAC GCC      432
His Glu Lys Pro Ser Asn Ile Lys Val Phe Ile His Glu Leu Asn Ala
        130                 135                 140

GGC AAC CAG CTC AGC CAC ATG TCG CCG ATC TAC ACC ATC GAG ATG GGC      480
Gly Asn Gln Leu Ser His Met Ser Pro Ile Tyr Thr Ile Glu Met Gly
145                 150                 155                 160

GAC GAG TTG CTG GCG AAG CTG GCG CGC GAT GCC ACC TTC TTC GTC AGG      528
Asp Glu Leu Leu Ala Lys Leu Ala Arg Asp Ala Thr Phe Phe Val Arg
                165                 170                 175

GCG CAC GAG AGC AAC GAG ATG CAG CCG ACG CTC GCC ATC AGC CAT GCC      576
Ala His Glu Ser Asn Glu Met Gln Pro Thr Leu Ala Ile Ser His Ala
        180                 185                 190

GGG GTC AGC GTG GTC ATG GCC CAG AAC CAG CCG CGC GGA AAG CGC          624
Gly Val Ser Val Val Met Ala Gln Asn Gln Pro Arg Arg Glu Lys Arg
            195                 200                 205

TGG AGC GAA TGG GCC AGC GGC AAG GTG TTG TGC CTG CTC GAC CCG CTG      672
Trp Ser Glu Trp Ala Ser Gly Lys Val Leu Cys Leu Leu Asp Pro Leu
210                 215                 220

GAC GGG GTC TAC AAC TAC CTC GCC CAG CAA CGC TGC AAC CTC GAC GAT      720
Asp Gly Val Tyr Asn Tyr Leu Ala Gln Gln Arg Cys Asn Leu Asp Asp
225                 230                 235                 240

ACC TGG GAA GGC AAG ATC TAC CGG GTG CTC GCC GGC AAC CCG GCG AAG      768
Thr Trp Glu Gly Lys Ile Tyr Arg Val Leu Ala Gly Asn Pro Ala Lys
                245                 250                 255

CAT GAC CTG GAC ATC AAA CCC ACG GTC ATC AGT GAA GAG CTG GAG TTT      816
His Asp Leu Asp Ile Lys Pro Thr Val Ile Ser Glu Glu Leu Glu Phe
        260                 265                 270

CCC GAG GGC GGC AGC CTG GCC GCG CTG ACC GCG CAC CAG GCT TGC CAC      864
Pro Glu Gly Gly Ser Leu Ala Ala Leu Thr Ala His Gln Ala Cys His
            275                 280                 285

CTG CCG CTG GAG ACT TTC ACC CGT CAT CGC CAG CCG CGC GGC TGG GAA      912
Leu Pro Leu Glu Thr Phe Thr Arg His Arg Gln Pro Arg Gly Trp Glu
290                 295                 300

CAA CTG GAG CAG TGC GGC TAT CCG GTG CAG CGG CTG GTC GCC CTC TAC      960
Gln Leu Glu Gln Cys Gly Tyr Pro Val Gln Arg Leu Val Ala Leu Tyr
305                 310                 315                 320

CTG GCG GCG CGG CTG TCG TGG AAC CAG GTC GAC CAG GTG ATC CGC AAC     1008
Leu Ala Ala Arg Leu Ser Trp Asn Gln Val Asp Gln Val Ile Arg Asn
                325                 330                 335

GCC CTG GCC AGC CCC GGC AGC GGC GGC GAC CTG GGC GAA GCG ATC CGC     1056
Ala Leu Ala Ser Pro Gly Ser Gly Gly Asp Leu Gly Glu Ala Ile Arg
        340                 345                 350

GAG CAG CCG GAG CAG GCC CGT CTG GCC CTG ACC CTG GCC GCC GCC GAG     1104
Glu Gln Pro Glu Gln Ala Arg Leu Ala Leu Thr Leu Ala Ala Ala Glu
            355                 360                 365

AGC GAG CGC TTC GTC CGG CAG GGC ACC GGC AAC GAC GAG GCC GGC GCG     1152
Ser Glu Arg Phe Val Arg Gln Gly Thr Gly Asn Asp Glu Ala Gly Ala
370                 375                 380

GCC AAC GCC GAC GTG GTG AGC CTG ACC TGC CCG GTC GCC GCC GGT GAA     1200
Ala Asn Ala Asp Val Val Ser Leu Thr Cys Pro Val Ala Ala Gly Glu
385                 390                 395                 400

TGC GCG GGC CCG GCG GAC AGC GGC GAC GCC CTG CTG GAG GCG AAC TAT     1248
Cys Ala Gly Pro Ala Asp Ser Gly Asp Ala Leu Leu Glu Ala Asn Tyr
                405                 410                 415

CCC ACT GGC GCG GAG TTC CTC GGC GAC GGC GGC GAC GTC AGC TTC AGC     1296
Pro Thr Gly Ala Glu Phe Leu Gly Asp Gly Gly Asp Val Ser Phe Ser
        420                 425                 430

ACC CGC GGC ACG CAG AAC TGG ACG GTG GAG CGG CTG CTC CAG GCG CAC     1344
Thr Arg Gly Thr Gln Asn Trp Thr Val Glu Arg Leu Leu Gln Ala His
            435                 440                 445
```

```
CGC CAA CTG GAG GAG CGC GGC TAT GTG TTC GTC GGC TAC CAC GGC ACC     1392
Arg Gln Leu Glu Glu Arg Gly Tyr Val Phe Val Gly Tyr His Gly Thr
        450                 455                 460

TTC CTC GAA GCG GCG CAA AGC ATC GTC TTC GGC GGG GTG CGC GCG CGC     1440
Phe Leu Glu Ala Ala Gln Ser Ile Val Phe Gly Gly Val Arg Ala Arg
465                 470                 475                 480

AGC CAG GAC CTC GAC GCG ATC TGG CGC GGT TTC TAT ATC GCC GGC GAT     1488
Ser Gln Asp Leu Asp Ala Ile Trp Arg Gly Phe Tyr Ile Ala Gly Asp
                485                 490                 495

CCG GCG CTG GCC TAC GGC TAC GCC CAG GAC CAG GAA CCC GAC GCA CGC     1536
Pro Ala Leu Ala Tyr Gly Tyr Ala Gln Asp Gln Glu Pro Asp Ala Arg
            500                 505                 510

GGC CGG ATC CGC AAC GGT GCC CTG CTG CGG GTC TAT GTG CCG CGC TCG     1584
Gly Arg Ile Arg Asn Gly Ala Leu Leu Arg Val Tyr Val Pro Arg Ser
        515                 520                 525

AGC CTG CCG GGC TTC TAC CGC ACC AGC CTG ACC CTG GCC GCG CCG GAG     1632
Ser Leu Pro Gly Phe Tyr Arg Thr Ser Leu Thr Leu Ala Ala Pro Glu
530                 535                 540

GCG GCG GGC GAG GTC GAA CGG CTG ATC GGC CAT CCG CTG CCG CTG CGC     1680
Ala Ala Gly Glu Val Glu Arg Leu Ile Gly His Pro Leu Pro Leu Arg
545                 550                 555                 560

CTG GAC GCC ATC ACC GGC CCC GAG GAG GAA GGC GGG CGC CTG GAG ACC     1728
Leu Asp Ala Ile Thr Gly Pro Glu Glu Glu Gly Gly Arg Leu Glu Thr
                565                 570                 575

ATT CTC GGC TGG CCG CTG GCC GAG CGC ACC GTG GTG ATT CCC TCG GCG     1776
Ile Leu Gly Trp Pro Leu Ala Glu Arg Thr Val Val Ile Pro Ser Ala
                580                 585                 590

ATC CCC ACC GAC CCG CGC AAC GTC GGC GGC GAC CTC GAC CCG TCC AGC     1824
Ile Pro Thr Asp Pro Arg Asn Val Gly Gly Asp Leu Asp Pro Ser Ser
            595                 600                 605

ATC CCC GAC AAG GAA CAG GCG ATC AGC GCC CTG CCG GAC TAC GCC AGC     1872
Ile Pro Asp Lys Glu Gln Ala Ile Ser Ala Leu Pro Asp Tyr Ala Ser
        610                 615                 620

CAG CCC GGC AAA CCG CCG CGC GAG GAC CTG AAG TAA                     1908
Gln Pro Gly Lys Pro Pro Arg Glu Asp Leu Lys
625                 630                 635

(2) INFORMATION FOR SEQ ID NO:2:

(i) SEQUENCE CHARACTERISTICS:
        (A) LENGTH: 635 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Glu His Trp Ser Tyr Trp Leu Arg Pro Gly Glu Ala Gly Gly Gly
1               5                   10                  15

Gly Ser Gly Gly Gly Ser Gly Gln Ala Phe Asp Leu Trp Asn Glu
            20                  25                  30

Cys Ala Lys Ala Cys Val Leu Asp Leu Lys Asp Gly Val Arg Ser Ser
                35                  40                  45

Arg Met Ser Val Asp Pro Ala Ile Ala Asp Thr Asn Gly Gln Gly Val
        50                  55                  60

Leu His Tyr Ser Met Val Leu Glu Gly Gly Asn Asp Ala Leu Glu Leu
65                  70                  75                  80
```

```
Ala Ile Asp Asn Ala Leu Ser Ile Thr Ser Asp Gly Leu Thr Ile Arg
                85                  90                  95

Leu Glu Gly Gly Val Glu Pro Asn Lys Pro Leu Arg Tyr Ser Tyr Thr
            100                 105                 110

Arg Gln Ala Arg Gly Arg Trp Ser Leu Asn Trp Leu Val Pro Ile Gly
        115                 120                 125

His Glu Lys Pro Ser Asn Ile Lys Val Phe Ile His Glu Leu Asn Ala
    130                 135                 140

Gly Asn Gln Leu Ser His Met Ser Pro Ile Tyr Thr Ile Glu Met Gly
145                 150                 155                 160

Asp Glu Leu Leu Ala Lys Leu Ala Arg Asp Ala Thr Phe Phe Val Arg
                165                 170                 175

Ala His Glu Ser Asn Glu Met Gln Pro Thr Leu Ala Ile Ser His Ala
            180                 185                 190

Gly Val Ser Val Val Met Ala Gln Asn Gln Pro Arg Arg Glu Lys Arg
        195                 200                 205

Trp Ser Glu Trp Ala Ser Gly Lys Val Leu Cys Leu Leu Asp Pro Leu
    210                 215                 220

Asp Gly Val Tyr Asn Tyr Leu Ala Gln Gln Arg Cys Asn Leu Asp Asp
225                 230                 235                 240

Thr Trp Glu Gly Lys Ile Tyr Arg Val Leu Ala Gly Asn Pro Ala Lys
                245                 250                 255

His Asp Leu Asp Ile Lys Pro Thr Val Ile Ser Glu Leu Glu Phe
            260                 265                 270

Pro Glu Gly Gly Ser Leu Ala Ala Leu Thr Ala His Gln Ala Cys His
        275                 280                 285

Leu Pro Leu Glu Thr Phe Thr Arg His Arg Gln Pro Arg Gly Trp Glu
    290                 295                 300

Gln Leu Glu Gln Cys Gly Tyr Pro Val Gln Arg Leu Val Ala Leu Tyr
305                 310                 315                 320

Leu Ala Ala Arg Leu Ser Trp Asn Gln Val Asp Gln Val Ile Arg Asn
                325                 330                 335

Ala Leu Ala Ser Pro Gly Ser Gly Gly Asp Leu Gly Glu Ala Ile Arg
            340                 345                 350

Glu Gln Pro Glu Gln Ala Arg Leu Ala Leu Thr Leu Ala Ala Ala Glu
        355                 360                 365

Ser Glu Arg Phe Val Arg Gln Gly Thr Gly Asn Asp Glu Ala Gly Ala
    370                 375                 380

Ala Asn Ala Asp Val Val Ser Leu Thr Cys Pro Val Ala Ala Gly Glu
385                 390                 395                 400

Cys Ala Gly Pro Ala Asp Ser Gly Asp Ala Leu Leu Glu Ala Asn Tyr
                405                 410                 415

Pro Thr Gly Ala Glu Phe Leu Gly Asp Gly Asp Val Ser Phe Ser
            420                 425                 430

Thr Arg Gly Thr Gln Asn Trp Thr Val Glu Arg Leu Leu Gln Ala His
        435                 440                 445

Arg Gln Leu Glu Glu Arg Gly Tyr Val Phe Val Gly Tyr His Gly Thr
    450                 455                 460

Phe Leu Glu Ala Ala Gln Ser Ile Val Phe Gly Gly Val Arg Ala Arg
465                 470                 475                 480

Ser Gln Asp Leu Asp Ala Ile Trp Arg Gly Phe Tyr Ile Ala Gly Asp
                485                 490                 495

Pro Ala Leu Ala Tyr Gly Tyr Ala Gln Asp Gln Glu Pro Asp Ala Arg
```

```
                        500                 505                 510
Gly Arg Ile Arg Asn Gly Ala Leu Leu Arg Val Tyr Val Pro Arg Ser
            515                 520                 525

Ser Leu Pro Gly Phe Tyr Arg Thr Ser Leu Thr Leu Ala Ala Pro Glu
    530                 535                 540

Ala Ala Gly Glu Val Glu Arg Leu Ile Gly His Pro Leu Pro Leu Arg
545                 550                 555                 560

Leu Asp Ala Ile Thr Gly Pro Glu Glu Gly Gly Arg Leu Glu Thr
                565                 570                 575

Ile Leu Gly Trp Pro Leu Ala Glu Arg Thr Val Val Ile Pro Ser Ala
            580                 585                 590

Ile Pro Thr Asp Pro Arg Asn Val Gly Gly Asp Leu Asp Pro Ser Ser
        595                 600                 605

Ile Pro Asp Lys Glu Gln Ala Ile Ser Ala Leu Pro Asp Tyr Ala Ser
    610                 615                 620

Gln Pro Gly Lys Pro Pro Arg Glu Asp Leu Lys
625                 630                 635

(2) INFORMATION FOR SEQ ID NO:3:

(i) SEQUENCE CHARACTERISTICS:
        (A) LENGTH: 1191 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 1...1188
        (D) OTHER INFORMATION:

(xi) SEQUENCE DESCRIPTION: SEQ ID NO:3:

ATG GAG CAC TGG TCC TAT TGG CTG CGC CCT GGA GAA GCT GGA GGA GGA           48
Met Glu His Trp Ser Tyr Trp Leu Arg Pro Gly Glu Ala Gly Gly Gly
 1               5                  10                  15

GGA TCC GGA GGA GGA GGA TCC GGT CAA GCT TTT GTT AAC GCC CAT ATG           96
Gly Ser Gly Gly Gly Gly Ser Gly Gln Ala Phe Val Asn Ala His Met
                20                  25                  30

GCC GAA GAG GGC GGC AGC CTG GCC GCG CTG ACC GCG CAC CAG GCT TGC          144
Ala Glu Glu Gly Gly Ser Leu Ala Ala Leu Thr Ala His Gln Ala Cys
            35                  40                  45

CAC CTG CCG CTG GAG ACT TTC ACC CGT CAT CGC CAG CCG CGC GGC TGG          192
His Leu Pro Leu Glu Thr Phe Thr Arg His Arg Gln Pro Arg Gly Trp
        50                  55                  60

GAA CAA CTG GAG CAG TGC GGC TAT CCG GTG CAG CGG CTG GTC GCC CTC          240
Glu Gln Leu Glu Gln Cys Gly Tyr Pro Val Gln Arg Leu Val Ala Leu
65                  70                  75                  80

TAC CTG GCG GCG CGG CTG TCG TGG AAC CAG GTC GAC CAG GTG ATC CGC          288
Tyr Leu Ala Ala Arg Leu Ser Trp Asn Gln Val Asp Gln Val Ile Arg
                85                  90                  95

AAC GCC CTG GCC AGC CCC GGC AGC GGC GGC GAC CTG GGC GAA GCG ATC          336
Asn Ala Leu Ala Ser Pro Gly Ser Gly Gly Asp Leu Gly Glu Ala Ile
            100                 105                 110

CGC GAG CAG CCG GAG CAG GCC CGT CTG GCC CTG ACC CTG GCC GCC GCC          384
Arg Glu Gln Pro Glu Gln Ala Arg Leu Ala Leu Thr Leu Ala Ala Ala
        115                 120                 125

GAG AGC GAG CGC TTC GTC CGG CAG GGC ACC GGC AAC GAC GAG GCC GGC          432
Glu Ser Glu Arg Phe Val Arg Gln Gly Thr Gly Asn Asp Glu Ala Gly
    130                 135                 140

GCG GCC AAC GCC GAC GTG GTG AGC CTG ACC TGC CCG GTC GCC GCC GGT          480
```

```
Ala Ala Asn Ala Asp Val Val Ser Leu Thr Cys Pro Val Ala Ala Gly
145                 150                 155                 160

GAA TGC GCG GGC CCG GCG GAC AGC GGC GAC GCC CTG CTG GAG CGC AAC      528
Glu Cys Ala Gly Pro Ala Asp Ser Gly Asp Ala Leu Leu Glu Arg Asn
                165                 170                 175

TAT CCC ACT GGC GCG GAG TTC CTC GGC GAC GGC GGC GAC GTC AGC TTC      576
Tyr Pro Thr Gly Ala Glu Phe Leu Gly Asp Gly Gly Asp Val Ser Phe
            180                 185                 190

AGC ACC CGC GGC ACG CAG AAC TGG ACG GTG GAG CGG CTG CTC CAG GCG      624
Ser Thr Arg Gly Thr Gln Asn Trp Thr Val Glu Arg Leu Leu Gln Ala
        195                 200                 205

CAC CGC CAA CTG GAG GAG CGC GGC TAT GTG TTC GTC GGC TAC CAC GGC      672
His Arg Gln Leu Glu Glu Arg Gly Tyr Val Phe Val Gly Tyr His Gly
    210                 215                 220

ACC TTC CTC GAA GCG GCG CAA AGC ATC GTC TTC GGC GGG GTG CGC GCG      720
Thr Phe Leu Glu Ala Ala Gln Ser Ile Val Phe Gly Gly Val Arg Ala
225                 230                 235                 240

CGC AGC CAG GAC CTC GAC GCG ATC TGG CGC GGT TTC TAT ATC GCC GGC      768
Arg Ser Gln Asp Leu Asp Ala Ile Trp Arg Gly Phe Tyr Ile Ala Gly
                245                 250                 255

GAT CCG GCG CTG GCC TAC GGC TAC GCC CAG GAC CAG GAA CCC GAC GCA      816
Asp Pro Ala Leu Ala Tyr Gly Tyr Ala Gln Asp Gln Glu Pro Asp Ala
            260                 265                 270

CGC GGC CGG ATC CGC AAC GGT GCC CTG CTG CGG GTC TAT GTG CCG CGC      864
Arg Gly Arg Ile Arg Asn Gly Ala Leu Leu Arg Val Tyr Val Pro Arg
        275                 280                 285

TCG AGC CTG CCG GGC TTC TAC CGC ACC AGC CTG ACC CTG GCC GCG CCG      912
Ser Ser Leu Pro Gly Phe Tyr Arg Thr Ser Leu Thr Leu Ala Ala Pro
    290                 295                 300

GAG GCG GCG GGC GAG GTC GAA CGG CTG ATC GGC CAT CCG CTG CCG CTG      960
Glu Ala Ala Gly Glu Val Glu Arg Leu Ile Gly His Pro Leu Pro Leu
305                 310                 315                 320

CGC CTG GAC GCC ATC ACC GGC CCC GAG GAG GAA GGC GGG CGC CTG GAG     1008
Arg Leu Asp Ala Ile Thr Gly Pro Glu Glu Glu Gly Gly Arg Leu Glu
                325                 330                 335

ACC ATT CTC GGC TGG CCG CTG GCC GAG CGC ACC GTG GTG ATT CCC TCG     1056
Thr Ile Leu Gly Trp Pro Leu Ala Glu Arg Thr Val Val Ile Pro Ser
            340                 345                 350

GCG ATC CCC ACC GAC CCG CGC AAC GTC GGC GGC GAC CTC GAC CCG TCC     1104
Ala Ile Pro Thr Asp Pro Arg Asn Val Gly Gly Asp Leu Asp Pro Ser
        355                 360                 365

AGC ATC CCC GAC AAG GAA CAG GCG ATC AGC GCC CTG CCG GAC TAC GCC     1152
Ser Ile Pro Asp Lys Glu Gln Ala Ile Ser Ala Leu Pro Asp Tyr Ala
    370                 375                 380

AGC CAG CCC GGC AAA CCG CCG CGC GAG GAC CTG AAG TAA                 1191
Ser Gln Pro Gly Lys Pro Pro Arg Glu Asp Leu Lys
385                 390                 395
```

(2) INFORMATION FOR SEQ ID NO:4:

(i) SEQUENCE CHARACTERISTICS:
        (A) LENGTH: 396 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

Met Glu His Trp Ser Tyr Trp Leu Arg Pro Gly Glu Ala Gly Gly Gly

```
 1               5                   10                  15
Gly Ser Gly Gly Gly Ser Gly Gln Ala Phe Val Asn Ala His Met
                20                  25              30
Ala Glu Glu Gly Gly Ser Leu Ala Ala Leu Thr Ala His Gln Ala Cys
            35                  40              45
His Leu Pro Leu Glu Thr Phe Thr Arg His Arg Gln Pro Arg Gly Trp
        50                  55              60
Glu Gln Leu Glu Gln Cys Gly Tyr Pro Val Gln Arg Leu Val Ala Leu
65                  70              75                  80
Tyr Leu Ala Ala Arg Leu Ser Trp Asn Gln Val Asp Gln Val Ile Arg
                85              90                  95
Asn Ala Leu Ala Ser Pro Gly Ser Gly Gly Asp Leu Gly Glu Ala Ile
            100                 105             110
Arg Glu Gln Pro Glu Gln Ala Arg Leu Ala Leu Thr Leu Ala Ala Ala
        115                 120             125
Glu Ser Glu Arg Phe Val Arg Gln Gly Thr Gly Asn Asp Glu Ala Gly
    130                 135             140
Ala Ala Asn Ala Asp Val Val Ser Leu Thr Cys Pro Val Ala Ala Gly
145                 150             155                 160
Glu Cys Ala Gly Pro Ala Asp Ser Gly Asp Ala Leu Leu Glu Arg Asn
                165             170                 175
Tyr Pro Thr Gly Ala Glu Phe Leu Gly Asp Gly Asp Val Ser Phe
            180             185                 190
Ser Thr Arg Gly Thr Gln Asn Trp Thr Val Glu Arg Leu Leu Gln Ala
        195             200                 205
His Arg Gln Leu Glu Glu Arg Gly Tyr Val Phe Val Gly Tyr His Gly
    210                 215             220
Thr Phe Leu Glu Ala Ala Gln Ser Ile Val Phe Gly Gly Val Arg Ala
225                 230             235                 240
Arg Ser Gln Asp Leu Asp Ala Ile Trp Arg Gly Phe Tyr Ile Ala Gly
                245             250                 255
Asp Pro Ala Leu Ala Tyr Gly Tyr Ala Gln Asp Gln Glu Pro Asp Ala
            260             265                 270
Arg Gly Arg Ile Arg Asn Gly Ala Leu Leu Arg Val Tyr Val Pro Arg
        275                 280             285
Ser Ser Leu Pro Gly Phe Tyr Arg Thr Ser Leu Thr Leu Ala Ala Pro
    290                 295             300
Glu Ala Ala Gly Glu Val Glu Arg Leu Ile Gly His Pro Leu Pro Leu
305                 310             315                 320
Arg Leu Asp Ala Ile Thr Gly Pro Glu Glu Gly Gly Arg Leu Glu
            325             330                 335
Thr Ile Leu Gly Trp Pro Leu Ala Glu Arg Thr Val Val Ile Pro Ser
        340                 345             350
Ala Ile Pro Thr Asp Pro Arg Asn Val Gly Gly Asp Leu Asp Pro Ser
    355                 360             365
Ser Ile Pro Asp Lys Glu Gln Ala Ile Ser Ala Leu Pro Asp Tyr Ala
    370                 375             380
Ser Gln Pro Gly Lys Pro Pro Arg Glu Asp Leu Lys
385                 390             395
```

(2) INFORMATION FOR SEQ ID NO:5:

(i) SEQUENCE CHARACTERISTICS:
        (A) LENGTH: 5 amino acids

```
            (B) TYPE: amino acid
            (C) STRANDEDNESS: single
            (D) TOPOLOGY: linear (xi) SEQUENCE DESCRIPTION: SEQ ID NO:5:

Gly Gly Gly Gly Ser
1               5

(2) INFORMATION FOR SEQ ID NO:6:

(i) SEQUENCE CHARACTERISTICS:
            (A) LENGTH: 14 amino acids
            (B) TYPE: amino acid
            (C) STRANDEDNESS: single
            (D) TOPOLOGY: linear (xi) SEQUENCE DESCRIPTION: SEQ ID NO:6:

Glu Gly Lys Ser Ser Gly Ser Gly Ser Glu Ser Lys Val Asp
1               5                   10

(2) INFORMATION FOR SEQ ID NO:7:

(i) SEQUENCE CHARACTERISTICS:
            (A) LENGTH: 18 amino acids
            (B) TYPE: amino acid
            (C) STRANDEDNESS: single
            (D) TOPOLOGY: linear (xi) SEQUENCE DESCRIPTION: SEQ ID NO:7:

Lys Glu Ser Gly Ser Val Ser Ser Glu Gln Leu Ala Gln Phe Arg Ser
1               5                   10                  15

Leu Asp
```